United States Patent [19]

Hanatani et al.

[11] Patent Number: 5,258,251
[45] Date of Patent: Nov. 2, 1993

[54] HYDRAZONE COMPOUND AND PHOTOSENSITIVE MATERIAL USING SAID COMPOUND

[75] Inventors: Yasuyuki Hanatani, Sakai; Hiroaki Iwasaki, Hirakata, both of Japan

[73] Assignee: Mita Industrial Co., Ltd., Osaka, Japan

[21] Appl. No.: 855,505

[22] Filed: Mar. 23, 1992

[30] Foreign Application Priority Data

Mar. 28, 1991 [JP] Japan ................................ 3-64983

[51] Int. Cl.$^5$ .......................................... G03G 15/02
[52] U.S. Cl. ........................................ 430/59; 430/73; 564/250; 564/251
[58] Field of Search ............... 564/250, 251; 430/58, 430/59, 73

[56] References Cited

U.S. PATENT DOCUMENTS

| | | | |
|---|---|---|---|
| 4,385,106 | 5/1983 | Sakai | 430/59 |
| 4,399,208 | 8/1983 | Takasu et al. | 430/59 |
| 4,666,809 | 5/1987 | Matsumoto et al. | 430/76 |
| 4,988,596 | 1/1991 | Ueda | 430/59 |

FOREIGN PATENT DOCUMENTS

| | | | |
|---|---|---|---|
| 0099552 | 2/1984 | European Pat. Off. | 564/251 |
| 345005A | 12/1989 | European Pat. Off. | 430/59 |
| 2-272571 | 11/1990 | Japan . | |

*Primary Examiner*—Allen J. Robinson
*Assistant Examiner*—Shailendra Kumar
*Attorney, Agent, or Firm*—Beveridge, DeGrandi, Weilacher & Young

[57] ABSTRACT

The present invention provides a hydrazone compound represented by the following general formula (1). This compound has higher hole mobility as compared with an electric charge transferring material such as the conventional hydrazone compound or the like. Accordingly, when this compound is contained in a photosensitive layer as the electric charge transferring material, there may be obtained an electrophotosensitive material excellent in sensitivity, charging ability and repeat characteristics.

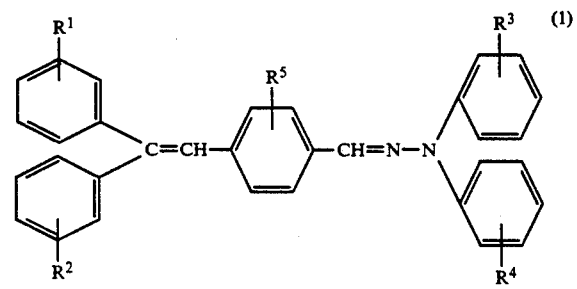

(wherein $R^1$, $R^2$, $R^3$, $R^4$ and $R^5$ are the same as or different from one another, and each is a hydrogen atom, a halogen atom, an alkyl group or an alkoxy group.)

9 Claims, No Drawings

HYDRAZONE COMPOUND AND PHOTOSENSITIVE MATERIAL USING SAID COMPOUND

BACKGROUND OF THE INVENTION

The present invention relates to a novel hydrazone compound, and also relates to a photosensitive material using such a compound.

As a photosensitive material in an image forming apparatus such as an electrophotographic copying apparatus, a printer or a facsimile, there has recently and widely been used an organic photosensitive material which is excellent in machinability and advantageous in production cost and which offers a great degree of freedom for design of performance.

For forming a copied image with the use of an electrophotosensitive material, the Carlson process is widely used. The Carlson process comprises the steps of uniformly charging a photosensitive material with electricity by corona discharge, exposing the charged photosensitive material to a document image, thereby to form an electrostatic latent image corresponding to the document image, developing the electrostatic latent image by a toner containing developer, thereby to form a toner image, transferring the toner image to a medium such as paper, fixing the toner image transferred to the medium, and cleaning the photosensitive material to remove toner remaining thereon after the toner image has been transferred. To form an image of high quality in the Carlson process, it is required that the electrophotosensitive material is excellent in charging and photosensitive characteristics and presents a low residual potential after exposed to light.

Conventionally, there have been known inorganic photoconductive materials such as selenium, cadmium sulfide and the like as electrophotosensitive materials. However, these inorganic photoconductive materials are toxic and need great production costs.

There has been proposed a so-called organic electrophotosensitive material using various organic substances in place of the above-mentioned inorganic substances. Such an organic photosensitive material has a photosensitive layer comprised of an electric charge generating material for generating electric charges by light exposure and an electric charge transferring material having a function of transferring the electric charges thus generated.

To meet various requirements for the organic electrophotosensitive material, it is necessary to properly select the electric charge generating material and the electric charge transferring material. As the electric charge transferring material, various organic compounds have been proposed and put on the market. By way of example, there has been known a hydrazone compound disclosed in Japanese Unexamined Patent Publication No. 272571/1990.

Referring to the electric charge transferring material according to the prior art, however, sensitivity and repeat characteristics are not sufficient.

SUMMARY OF THE INVENTION

It is an object of the present invention to provide a hydrazone compound suitable for an electric charge transferring material.

It is another object of the present invention to provide an electrophotosensitive material excellent in sensitivity and repeat characteristics.

The hydrazone compound of the present invention is represented by the following general formula (1):

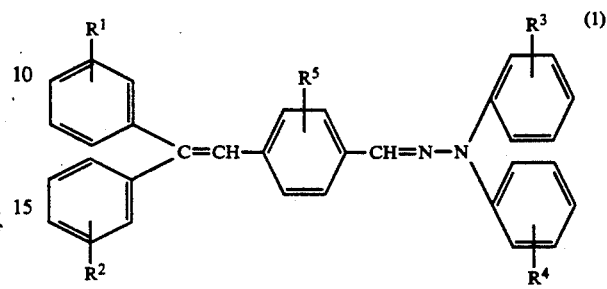

(wherein $R^1$, $R^2$, $R^3$, $R^4$ and $R^5$ are the same as or different from one another, and each is a hydrogen atom, a halogen atom, an alkyl group or an alkoxy group.)

The hydrazone compound of the present invention is effective as the electric charge transferring material, in particular, as a hole transferring material and has higher hole mobility as compared with the electric charge transferring material such as the hydrazone compound according to the prior art, or the like.

A photosensitive material containing the hydrazone compound (1) is excellent in sensitivity and charging ability and has high repeat characteristics.

DETAILED DESCRIPTION OF THE INVENTION

Examples of the alkyl group include a lower alkyl group having 1 to 6 carbon atoms, methyl, ethyl, propyl, isopropyl, butyl, isobutyl, t-butyl, pentyl and hexyl groups.

Examples of the alkoxy group include a lower alkoxy group having 1 to 6 carbon atoms in its alkyl portion, methoxy, ethoxy, isopropoxy, butoxy, t-butoxy and hexyloxy groups.

Examples of the halogen atom include chlorine, iodine, bromine and fluorine.

As specific examples of the hydrazone compound represented by the general formula (1), the following compounds (11) to (23) are mentioned.

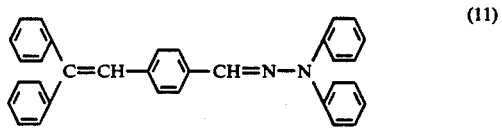

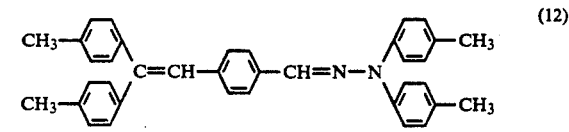

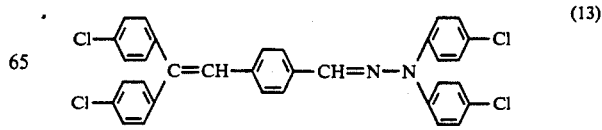

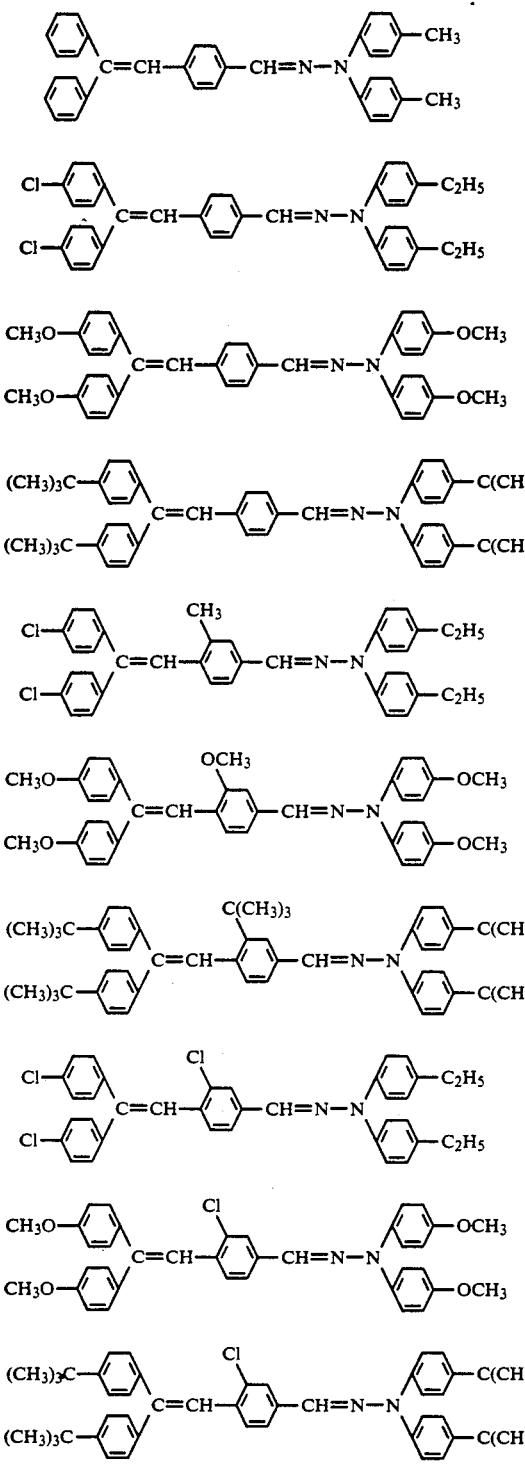

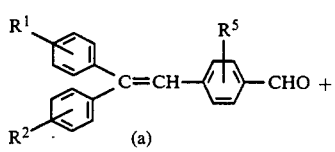

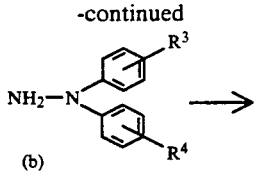

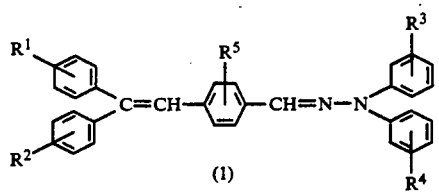

(wherein $R^1$, $R^2$, $R^3$, $R^4$ and $R^5$ are the same as mentioned above.)

An aldehyde compound of the formula (a) and a compound of the formula (b) are reacted in a suitable acidic solvent to which acetic acid and the like are added, thereby to give the hydrazone compound (1) of the present invention. Reaction is carried out in the solvent at 10° to 25° C. Examples of the solvent include ether, tetrahydrofuran, dioxane and the like.

The compound of the general formula (1) in accordance with the present invention may be contained, in a binding resin, alone or in combination with the other conventional electric charge transferring material, thereby to form a photosensitive layer. Examples of the conventional electric charge transferring material include nitrogen-containing cyclic compounds and condensed polycyclic compounds which include oxadiazole compounds such as 2,5-di(4-methylaminophenyl)-1,3,4-oxadiazole and the like, styryl compounds such as 9-(4-diethylaminostyryl) anthracene and the like, carbazole compounds such as polyvinyl carbazole and the like, pyrazoline compounds such as 1-phenyl-3-(p-dimethylaminophenyl)pyrazole and the like, triphenylamine compounds, indole compounds, oxazole compounds, isooxazole compounds, thiazole compounds, thiadiazole compounds, imidazole compounds, pyrazole compounds, triazole compounds and the like. These examples of the electric charge transferring material may be used alone or in combination of plural types. When there is used the electric charge transferring material having film-forming properties such as polyvinyl carbazole or the like, a binding resin is not necessarily required.

The compound of the general formula (1) may be used for a photosensitive material of the so-called single- or multi-layer type.

To form a single-layer type photosensitive material, there may be formed, on a conductive substrate, a photosensitive layer containing the compound of the general formula (1) serving as the electric charge transferring material, an electric charge generating material, a binding resin and the like.

To form a multi-layer type photosensitive material, an electric charge generating layer containing an electric charge generating material is formed on the conductive substrate, and the electric charge transferring layer containing the compound of the general formula (1) serving as the electric charge transferring material is then formed on the electric charge generating layer. On the contrary, the electric charge generating layer may be formed on the electric charge transferring layer.

The compound of the general formula (1) may be composed by the following reaction formula (see C. Mannich et al., Ber., 69, 2106, 2112 (1936)):

Examples of the electric charge generating material include selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon compounds, pyrrolopyrrole compounds and the like, which have conventionally been used. These examples may be used alone or in combination of plural types.

As the binding resin, any of a variety of resins may be used. Examples of the binding resin include various polymers which include: thermoplastic resins such as a styrene polymer, a styrene-butadiene copolymer, a sytrene-acrylonitrile copolymer, a styrene-maleic acid copolymer, an acrylic copolymer, a styrene-acrylic acid copolymer, polyethylene, an ethylene vinyl acetate copolymer, chlorinated polyethylene, polyvinyl chloride, polypropylene, a vinyl chloride/vinyl acetate copolymer, polyester, alkyd resin, polyamide, polyurethane, polycarbonate, polyarylate, polysulfon, dialyl phthalate resin, ketone resin, polyvinyl butyral resin, polyether resin and the like; crosslinking thermosetting resins such as silicone resin, epoxy resin and the like; photosetting resins such as epoxy-acrylate, urethane-acrylate and the like. These polymers may be used alone or in combination of plural types.

Examples of a solvent for dissolving the electric charge generating material, the electric charge transferring material and the binding resin to prepare a coating solution include: alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, carbon tetrachloride, chlorobenzene and the like; ethers such as dimethyl ether, diethyl ether, tetrahydrofuran, ethylene glycol dimethyl ether, diethylene glycol dimethyl ether and the like; ketones such as acetone, methylethyl ketone, cyclohexanone and the like; esters such as ethyl acetate, methyl acetate and the like; dimethylformaldehyde; dimethylformamide; dimethylsulfoxide and the like. These solvents may be used alone or in combination of plural types.

To improve the electric charge generating layer in sensitivity, there may be used a conventional sensitizer such as tert-phenyl, halonaphtoquinone, acenaphthylene or the like, together with the electric charge generating material.

To improve the electric charge transferring and generating materials in dispersibility, applicability and the like, there may be used a surfactant, a levelling agent and the like.

Examples of the conductive substrate include: single metal such as aluminium, copper, tin, platinum, silver, vanadium, molybdenum, chromium, cadmium, titanium, nickel, paradium, indium, stainless copper, brass and the like; plastic material vapor-deposited or laminated with any of the metals above-mentioned; glass material coated with aluminium iodide, tin oxide, indium oxide or the like.

The conductive substrate may be made in the form of a sheet or a drum. The substrate itself may be conductive or only the surface of the substrate may be conductive. Preferably, the substrate has a sufficient mechanical strength when used.

In the multi-layer type photosensitive material, the electric charge generating material forming the electric charge generating layer and the binding resin may be used at a variety of ratios. Preferably 5 to 500 parts by weight and more preferably 10 to 250 parts by weight of the electric charge generating material may be used for 100 parts by weight of the binding resin.

The thickness of the electric charge generating layer is optional, but is preferably from 0.01 to 5 $\mu$m and more preferably from 0.1 to 3 $\mu$m.

The compound (electric charge transferring material) of the general formula (1) forming an electric charge transferring layer and the binding resin may be used at a variety of ratios. Preferably 10 to 500 parts by weight and more preferably 25 to 200 parts by weight of the compound of the general formula (1) may be used for 100 parts by weight of the binding resin such that electric charges generated on the electric charge generating layer can easily be transferred by light radiation.

The thickness of the electric charge transferring layer is preferably from 2 to 100 $\mu$m and more preferably from 5 to 30 $\mu$m.

In the single-layer type photosensitive material, preferably 2 to 20 parts by weight and more preferably 3 to 15 parts by weight of the electric charge generating material, and preferably 40 to 200 parts by weight and more preferably 50 to 150 parts by weight of the compound of the general formula (1) (electric charge transferring material) may be used for 100 parts by weight of the binding resin. The thickness of the single-layer type photosensitive layer is preferably from 10 to 50 $\mu$m and more preferably from 15 to 30 $\mu$m.

When the photosensitive layer including the electric charge generating layer and the electric charge transferring layer is formed with coating means, the electric charge generating material or electric charge transferring material and the binding resin may be dispersed and mixed with the use of any of conventional methods, for example, a roll mill, a ball mill, an atriter, a paint shaker, a supersonic dispenser or the like, then to prepare a coating-solution.

EXAMPLES

The following description will discuss in detail the present invention with reference to examples and comparative examples thereof.

(1) Synthesis Examples of Electric Charge Transferring Material

Example 1

Synthesis of a compound represented by the formula (11)

2.84 g of an aldehyde compound of the following formula (23) and 1.84 g of diphenyl hydrazine $(C_6H_5)_2N-NH_2$ were agitated and reacted at a room temperature in an acidic solvent (60 ml) to which acetic acid is added, thereby to prepare a compound of the formula (11).

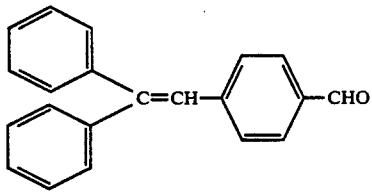

(23)

This compound had a yield of 77% and a melting point of 203° to 205° C. The following shows the results of elemental analysis.

In $C_{33}H_{26}N_2$: Calculation Values—C:87.96%, H:5.82%, N:6.22%; Measured Values—C:87.91%, H:5.80%, N:6.19%.

Each compound was prepared by using suitable starting materials in the same manner as in Example 1. The compounds thus obtained are as follows.

Example 2

Compound of the formula (12)

This compound had a melting point of 210° to 213° C. The following shows the results of elemental analysis.

In $C_{37}H_{34}N_2$: Calculation Values—C:87.71%, H:6.76%, N:5.53%; Measured Values—C:87.66%, H:6.78%, N:5.50%.

Example 3

Compound of the formula (13)

This compound had a melting point of 220° to 223° C. The following shows the results of elemental analysis.

In $C_{33}H_{22}N_2Cl_4$: Calculation Values—C:67.36%, H:3.77%, N:4.76%; Measured Values—C:67.29%, H:3.80%, N:4.72%.

(2) Preparation of Electrophotosensitive Material

Preparation of Multi-Layer Type Electrophotosensitive Material

Examples 4 to 6 and Comparative Example 1

2 Parts by weight of the electric charge generating material of the following formula (A), 1 part by weight of a polyvinyl butyral resin ("S-lecBH-5" manufactured by Sekisui Kagaku Kogyo Co., Ltd.) and 120 parts by weight of tetrahydrofuran were dispersed for 2 hours by means of a paint shaker using zirconia beads (having a diameter of 2 mm). The dispersing solution thus prepared was applied, by means of a wire bar, to an aluminium sheet, which was then dried at 100° C. for 1 hour. Thus, an electric charge generating layer with a thickness of 0.5 μm was formed.

1 Part by weight of the electric charge transferring material and 1 part by weight of a polycarbonate resin ("Z-200" manufactured by Mitsubishi Gas Kagaku Kogyo Co., Ltd.) were dissolved in 9 parts by weight of toluene. The solution thus prepared is applied, by means of the wire bar, to the electric charge generating layer, which was then dried at 100° C. for 1 hour. Thus, an electric charge transferring layer with a thickness of 22 μm was formed. The electric charge transferring materials used in Examples 4 to 6 are indicated at compound numbers shown in the above-mentioned specific examples in Table 1. The electric charge transferring material (24) used in Comparative Example 1 is a compound represented by the following formula (24).

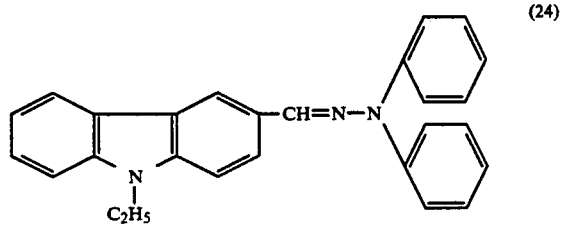

(24)

Preparation of Single-Layer Type Electrophotosensitive Material

Examples 7 to 9 and Comparative Example 2

1 Part by weight of the electric charge generating material of the formula (A) and 60 parts by weight of tetrahydrofuran were dispersed for 2 hours by means of a paint shaker using zirconia beads (having a diameter of 2 mm). To the dispersing solution thus prepared are added 50 parts by weight of a tetrahydrofuran solution of a polycarbonate resin having 20% by weight of a solid content ("Z-200" manufactured by Mitsubishi Gas Kagaku Kogyo Co., Ltd.) and 10 parts by weight of the electric charge transferring material, which were further dispersed for 1 hour. The dispersing solution thus prepared was applied, by means of a wire bar, to an aluminium sheet, which was then dried at 100° C. for 1 hour. Thus, a photosensitive layer with a thickness of 20 μm was formed. The electric charge transferring materials used in Examples 7 to 9 and Comparative Example 2 were indicated at respective compound numbers in the same manner as in the above-mentioned Examples shown in Table 1.

(3) Evaluation of the Electrophotosensitive Material

The surface potential, half-life light exposure ($E_{\frac{1}{2}}$) and residual potential of the photosensitive material obtained in the above-mentioned Examples and Comparative Examples were measured by means of an evaluation tester ("EPA8100" manufactured by Kawaguchi Denki Co., Ltd.).

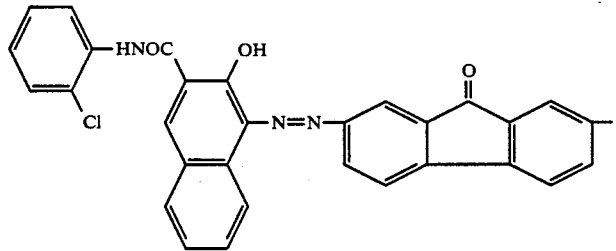

(A)

Measuring conditions are as follows.
Light Intensity: 50 lux

Exposure Intensity: 1/15 second

Surface Potential: A flowing current value was adjusted so as to approximate (±)700 V.

Light Source: Tungsten lamp

Electrical Removal: 200 lux

Measurement of Residual Potential: Measurement was started after exposure continued for 0.2 second.

The test results of the Examples 4 to 6 and Comparative Example 1 and those of the Examples 7 to 9 and Comparative Example 2 are shown in Tables 1 and 2, respectively.

TABLE 1

| | Electric charge transferring material | Surface potential (V) | $E_{\frac{1}{2}}$ (lux. sec) | Residual potential (V) |
|---|---|---|---|---|
| Example 4 | 12 | −705 | 1.18 | −120 |
| Example 5 | 11 | −701 | 1.15 | −115 |
| Example 6 | 13 | −700 | 1.20 | −124 |
| Comparative Example 1 | 21 | −702 | 1.88 | −150 |

TABLE 2

| | Electric charge transferring material | Surface potential (V) | $E_{\frac{1}{2}}$ (lux. sec) | Residual potential (V) |
|---|---|---|---|---|
| Example 7 | 11 | +700 | 2.60 | +160 |
| Example 8 | 12 | +702 | 2.58 | +158 |
| Example 9 | 13 | +705 | 2.61 | +165 |
| Comparative Example 2 | 21 | +700 | 3.00 | +180 |

As seen from these test results, the photosensitive layer of each of Examples has almost the same surface potential as in Comparative Examples, but is more excellent in half-life light exposure and residual potential and has its sensitivity remarkably improved.

What is claimed is:

1. A photosensitive material comprising:

a conductive substrate;

a photosensitive layer on the conductive substrate, which photosensitive layer contains a hydrazone compound as an electric charge transferring material, wherein the hydrazone compound is represented by the following formula:

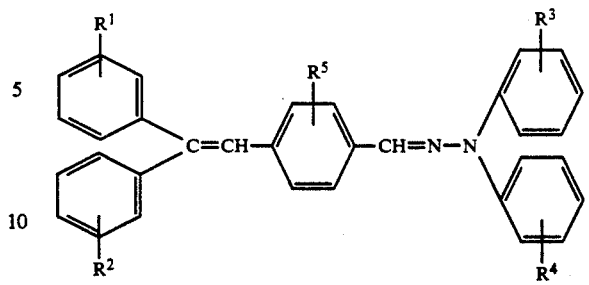

wherein $R^1$, $R^2$, $R^3$, $R^4$ and $R^5$ are the same or different from one another, and each is a hydrogen atom, a halogen atom, an alkyl group or an alkoxy group.

2. The photosensitive material according to claim 1, wherein the photosensitive layer is a multi-layer type photosensitive layer including an electric charge transferring layer which includes the hydrazone compound as the electric charge transferring material, and an electric charge generating layer, which layers are laminated mutually.

3. The photosensitive material according to claim 2, wherein the electric charge transferring layer of the multi-layer type photosensitive layer further includes a binding resin, and the electric charge transferring layer contains 25 to 200 parts by weight of said hydrazone compound for 100 parts by weight of the binding resin.

4. The photosensitive material according to claim 3, wherein the electric charge generating layer further includes a binding resin for the electric charge generating layer, wherein the electric charge generating layer contains, for 100 parts of the binding resin for the electric charge generating layer, 5 to 500 parts by weight of one or more kinds of an electric charge generating material selected from selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon-compounds, and pyrrolopyrrole compounds.

5. The photosensitive material according to claim 4, wherein the electric charge generating material is an azo compound.

6. The photosensitive material according to claim 1, wherein the photosensitive layer is a single-layer type photosensitive layer comprised of an electric charge transferring material, an electric charge generating material and a binding resin.

7. The photosensitive material according to claim 6, wherein the single-layer type photosensitive layer contains 40 to 200 parts by weight of said hydrazone compound for 100 parts by weight of the binding resin.

8. The photosensitive material according to claim 7, wherein the single-layer type photosensitive layer contains, for 100 parts by weight of the binding resin, 2 to 20 parts by weight of one or more kinds of an electric charge generating material selected from selenium, selenium-tellurium, selenium-arsenic, amorphous silicon, pyrylium salt, azo compounds, disazo compounds, phthalocyanine compounds, anthanthrone compounds, indigo compounds, triphenylmethane compounds, threne compounds, toluidine compounds, pyrazoline compounds, perylene compounds, quinacridon compounds, and pyrrolopyrrole compounds.

9. The photosensitive material according to claim 8, wherein the electric charge generating material is an azo compound.

* * * * *